(12) United States Patent
Yardley et al.

(10) Patent No.: US 7,291,646 B2
(45) Date of Patent: Nov. 6, 2007

(54) ETHERS OF O-DESMETHYL VENLAFAXINE

(75) Inventors: John P. Yardley, King of Prussia, PA (US); Magid A. Abou-Gharbia, Exton, PA (US); John W. Ullrich, Exton, PA (US)

(73) Assignee: Wyeth, Madison, NJ (US)

( * ) Notice: Subject to any disclaimer, the term of this patent is extended or adjusted under 35 U.S.C. 154(b) by 328 days.

(21) Appl. No.: 10/692,542

(22) Filed: Oct. 24, 2003

(65) Prior Publication Data

US 2004/0147601 A1  Jul. 29, 2004

Related U.S. Application Data

(60) Continuation-in-part of application No. 10/315,699, filed on Dec. 10, 2002, which is a division of application No. 09/989,000, filed on Nov. 21, 2001, now Pat. No. 6,503,942, which is a division of application No. 09/722,193, filed on Nov. 21, 2000, now Pat. No. 6,348,494.

(60) Provisional application No. 60/240,922, filed on Nov. 24, 1999.

(51) Int. Cl.
*A61K 31/22* (2006.01)
*C07C 211/00* (2006.01)

(52) U.S. Cl. ...................... 514/546; 564/305
(58) Field of Classification Search ........... 564/305; 514/546
See application file for complete search history.

(56) References Cited

U.S. PATENT DOCUMENTS

| | | | |
|---|---|---|---|
| 4,521,533 A | 6/1985 | Hamanaka et al. | |
| 4,535,186 A | 8/1985 | Husbands et al. | |
| 4,673,679 A | 6/1987 | Aungst et al. | |
| 5,506,270 A * | 4/1996 | Upton et al. | 514/730 |
| 5,530,013 A | 6/1996 | Husbands et al. | |
| 5,554,383 A | 9/1996 | Dodman | |
| 5,788,986 A | 8/1998 | Dodman | |

FOREIGN PATENT DOCUMENTS

| | | |
|---|---|---|
| EP | 0 639 374 | 6/1994 |
| EP | 0 654 264 | 11/1994 |
| JP | 07070317 | 3/1995 |
| WO | WO99/55694 | 11/1999 |
| WO | WO 00/32555 | 6/2000 |
| WO | WO 00/32556 | 6/2000 |

OTHER PUBLICATIONS

Hcaplus 142:16872.*
Hcaplus 142:290514.*
Hcaplus 134:65678.*
Hcaplus 132:44393.*
PubMed ID: 7729333.*
Bundgaard, Hans, Design of prodrugs, Elsevier, Amsterdam, p. 5.*
Hcaplus 129:239318.*
PubMed 16034979.*
PubMed ID: 15162896.*
John P. Yardley et al., J. Med. Chem., 1990, 2899-2905, 33.
Chemical Abstracts 124:86603n "Carbamate and urea derivatives with insect juvenile hormone activity, method for their production, and insectidal agents," (1996) 124(7):1274.
Grothe et al., "Treatment of Pain Syndromes with Venlafaxine," *Pharmacotherapy* (2004) 24(5):621-629.
Thor "Targeting Serotonin and Norepinephrine Receptors in Stress Urinary Incontinence," *International Journal of Gynecology and Obsterics* (2004) 86(Suppl 1):S38-S52.
Nutt et al., "Potential Applications of Venlafaxine," *Rev Contemp Pharmacother* (1998) 9:321-331.
Schatzberg "New Indications for Antidepressants," *J Clin Psychiatry* (2000) 61(Suppl 11):9-17.
Sarrto et al., "Antidepressants for Neuropathic Pain," *The Cochrane Collaboration* (2005) 4:1-83.
Ninan, Philip T., "Use of Venlafaxine in other psychiatric disorders", Depression and Anxiety, vol. 12, supplement 1:90-94 (2000).
Sally Freeman et al., "Prodrug Design for Phosphates and Phosphonates", *Caplus English Abstract DN* (1997) 128:79859.
Loftsson Thorsteinn et al., "Synthesis and Hydrolysis of Some Pivaloyloxymethyl and Pivaloyl Derivatives of Phenolic Compounds", *English Abstract Caplus DN* (1982) 98:59808.

* cited by examiner

*Primary Examiner*—Bernard Dentz
*Assistant Examiner*—Binta Robinson
(74) *Attorney, Agent, or Firm*—Rebecca R. Barrett; Pepper Hamilton LLP

(57) ABSTRACT

This invention provides O-α-acyloxyalkyl ethers of the venlafaxine metabolite 4-[2-(Dimehtylamino-1-(1-hydroxycyclohexyl)ethyl]phenol, represented by Formula (I):

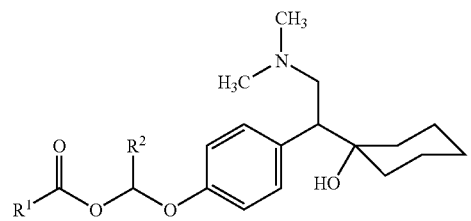

wherein the variables $R^1$ and $R^2$ are defined herein, and where the configuration at the steriogenic center (*) may be R, S, or RS (the racemate).

2 Claims, No Drawings

ETHERS OF O-DESMETHYL VENLAFAXINE

This is a continuation-in-part of U.S. Ser. No. 10/315,699 filed Dec. 10, 2002, which is a divisional of U.S. Ser. No. 09/989,000 filed on Nov. 21, 2001, now U.S. Pat. No. 6,503,942, which is a divisional of U.S. Ser. No. 09/722,193 filed on Nov. 21, 2000, now U.S. Pat. No. 6,348,494.

FIELD OF THE INVENTION

This invention provides O-α-acyloxyalkyl ethers of 4-[2-(Dimethylamino-1-(1-hydroxycyclohexyl)ethyl]phenol, as well as pharmaceutical compositions and uses thereof.

BACKGROUND OF THE INVENTION

Various patents and literature references describe the biological activities of venlafaxine, and its salts and analogs. Venlafaxine hydrochloride tablets are marketed by Wyeth-Ayerst Laboratories as EFFEXOR.

The absolute configuration of the (+) enantiomer of venlafaxine was established as S by a single crystal X-ray analysis of the hydrobromide salt and the anomalous dispersion technique (Yardley et al., J. Med. Chem., 1990, 33, 2899).

(R/S)-1-[2-(dimethylamino)-1-(4-methoxyphenyl)ethyl]cyclohexanol and its metabolites 1-[2-(dimethylamino)-1-(4-hydroxyphenyl)ethyl]cyclohexanol and 1-[1-(4-methoxyphenyl)-2-(methylamino)ethyl]cyclohexanol are disclosed and claimed in U.S. Pat. No. 4,535,186 (Husbands et al.). U.S. Pat. No. 5,530,013 (Husbands et al.) claims the use of venlafaxine in the inducement of cognition enhancement. U.S. Pat. No. 5,506,270 (Upton et al.) claims venlafaxine's use in methods of treating hypothalamic amenorrhea in non-depressed women.

U.S. Pat. No. 5,788,986 (Dodman) and U.S. Pat. No. 5,554,383 (Dodman) teaches and claims the use of serotonin reuptake inhibitors in modifying the behavior of dogs.

DETAILED DESCRIPTION OF THE INVENTION

This invention provides pharmaceutically active O-α-acyloxyalkyl ethers of the venlafaxine metabolite 4-[2-(Dimethylamino-1-(1-hydroxycyclohexyl)ethyl]phenol ("O-Desmethyl venlafaxine" or "ODV") having the structural formula I

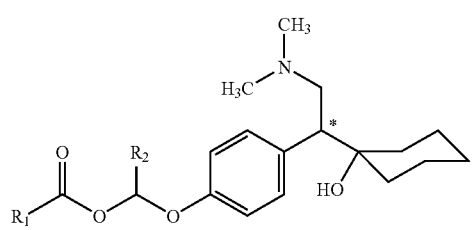

wherein
the configuration at the steriogenic center (*) may be R, S, or RS (the racemate);

$R_1$ is selected from $C_1$–$C_6$ alkyl, $C_1$–$C_6$ alkoxy, $C_3$–$C_6$ cycloalkyl, or the moiety:

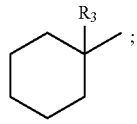

$R_2$ is selected from H, or $C_1$–$C_6$ alkyl; or,
$R_1$ and $R_2$ may be concatenated such that

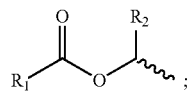

form a moiety having formula (b):

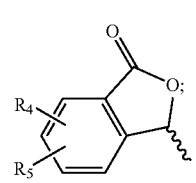

R3 is selected from H or $C_1$–$C_6$ alkyl; and
R4 and R5 are independently selected from H, $C_1$–$C_6$ alkyl, $C_3$–$C_6$ cycloalkyl, $C_1$–$C_6$ alkoxy, $C_1$–$C_6$ thioalkoxy, —CN, —OH, —CF$_3$, —OCF$_3$, halogen, —NH$_2$, —NO$_2$, or —N(CH$_3$)$_2$, or pharmaceutically acceptable salts or hydrates thereof.

In some preferred embodiments of the present invention R1 is t-butyl, methoxy, or isobenzofuranone.

In other preferred embodiments of the invention R2 is C1–C3 alkyl and in still more preferred embodiments of the invention R2 is methyl.

Specific examples of compounds of Formula I include:
2,2-dimethyl-propionic acid 4-[2-dimethylamino-1-(hydroxy-cyclohexyl)-ethyl]-phenoxymethylester;
Propionic acid 1-{4-[2-dimethylamino-1-(1-hydroxy-cyclohexyl-ethyl]-phenoxy}-ethyl ester;
[2-[4-(2,2-Dimethyl-propionyloxymethoxy)-phenyl]-2-(1-hydroxy-cyclohexyl)-ethyl]-dimethyl-ammonium; 3-carboxy-acrylate; and
3-{4-[2-dimethylamino-1-(1-hydroxy-cyclohexyl)-ethyl]-phenoxy}-3H-isobenzofuran-1-one.

Particularly, this invention provides compounds and/or compositions of both the O-α-acyloxyalkyl R-ether of Formula I and the O-α-acyloxyalkyl S-ether of Formula I, both being substantially free of the other. In addition, the invention provides the O-α-acyloxyalkyl RS-ether of 4-[2-(Dimethylamino)-1-(1-hydroxycyclohexyl)ethyl]-phenol of Formula I.

Substantially free, as used herein means the compound or composition is made up of significantly greater proportion of the desired isomer than of the optical antipode. In a preferred embodiment of the invention, "substantially free" means that the compound or composition is made up of at least about 90% of the desired isomer and about 10% or less of the optical antipode. In still more preferred embodiments of the present invention, the compound or composition is made up of at least about 95% of the desired isomer and about 5% or less of the optical antipode. In yet further embodiments of the present invention the compound or composition is made up of at least about 99% of the desired isomer and about 1% or less of the optical antipode. Preferably the characterized or separated enantiomer will exhibit physical properties of a fully characterized compound, i.e. a uniform melting point and a uniform rotation of plane-polarized light in a polarimeter. Most preferably, the enantiomers will be recrystallized to analytical purity.

$C_1$–$C_6$ alkyl as used herein, such as in the definition of $R_1$, includes straight, branched chain alkyl groups within the specified range of carbon atoms.

Halogen, as used herein refers to chlorine, bromine, iodine and fluorine.

Pharmaceutically acceptable salts refer to salts prepared from pharmaceutically acceptable acids, including inorganic acids and organic acids, such as, but not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, mitric, pamoic, pantothenic, phosphoric, succinic, sulfuric, tartaric, p-toluenesulfonic and the like.

Compounds of the invention are readily prepared by methods known in the art, for instance, as described by Bodor, et al., *J. Org. Chem.*(48) 5280–5284 (1983).

The appropriate R-, S-, or (R/S)-4-[2-(Dimethylamino-1-(1-hydroxycyclohexyl)ethyl]phenol is reacted with the appropriate O-α-acyloxyalkyl halide (examples: pivaloyloxymethyl chloride, 3-bromophthalide, iodomethyl pivalate) (Scheme Ia) or (acyloxy)benzyl α-halide (Scheme Ib) in an inert solvent (acetonitrile, tetrahydrofuran, dimethylformamide) in the presence of an alkali metal carbonate (sodium or potassium carbonate) or transition metal carbonate (silver carbonate) in accordance with Schemes Ia and Ib.

Scheme Ia

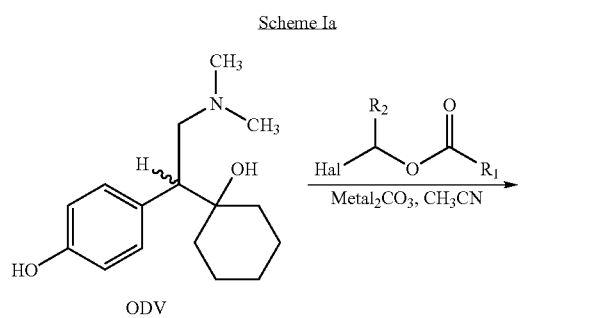

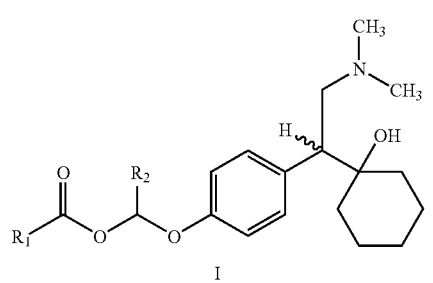

I

Scheme Ib

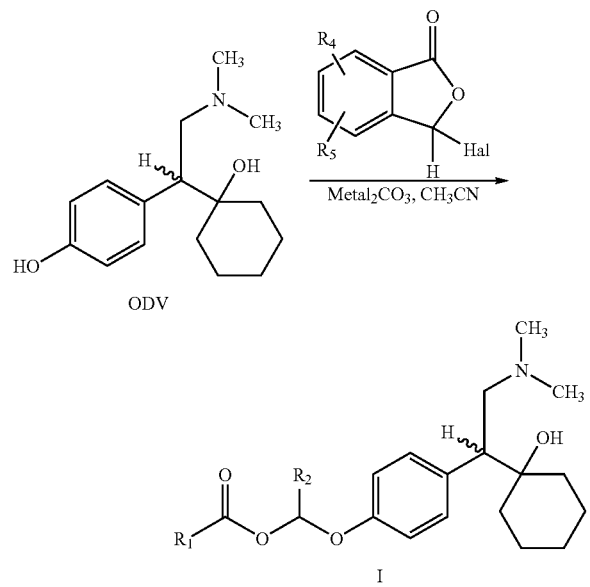

I wherein $R_1$ is selected from $C_1$–$C_6$ alkyl, $C_1$–$C_6$ alkoxy, $C_3$–$C_6$ cycloalkyl, or the moiety:

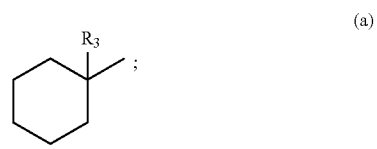

(a)

$R_2$ is selected from H, or $C_1$–$C_6$ alkyl, $C_3$–$C_6$ cycloalkyl;
R3 is selected from H or $C_1$–$C_6$ alkyl; and
R4 and R5 are independently selected from H, $C_1$–$C_6$ alkyl, $C_3$–$C_6$ cycloalkyl, $C_1$–$C_6$ alkoxy, $C_1$–$C_6$ thioalkoxy, —CN, —OH, —CF$_3$, —OCF$_3$, halogen, —NH$_2$, —NO$_2$, or mono or dialkylamino wherein each alkyl group has 1 to 6 carbon atoms.

In some preferred embodiments of the invention increased yield may be obtained by reacting the appropriate R-, S-, or (R/S)-4-[2-(Dimethylamino-1-(1-hydroxycyclohexyl)ethyl]phenol with the appropriate O-α-acyloxyalkyliodide in an inert solvent (acetonitrile, tetrahydrofuran, dimethylformamide) in the presence of alkali metal carbonate such as potassium carbonate, or transition metal carbonate such as silver carbonate. Most preferred is the use of O-α-acyloxyalkyliodide in the presence of silver carbonate at low temperatures in the range of approximately 0–5° C.

In a minor modification, compounds of formula I wherein R1 and R2 are concatenated to form

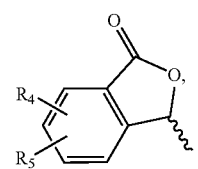

and one or both of $R_4$ and $R_5$ are $NH_2$, can be obtained by catalytic reductions, such as with palladium catalysts, from corresponding analogs wherein $R_4$ or $R_5$ are $NO_2$.

Racemic 1-[2-(dimethylamino)-1-(4-hydroxyphenyl) ethyl]cyclohexanol can be produced as described in Example 26 of U.S. Pat. No. 4,535,186 (Husbands et al.), which is incorporated herein by reference. It will be understood that the enantiomers may be separated from each other by standard resolution techniques known in the art.

Alternatively, these R and S enantiomers may be obtained by O-demethylation of the separated enantiomers of venlafaxine using either boron tribromide or ethane thiol anion.

O-α-acyloxyalkyl ethers of Formula I and their pharmaceutically useful salts and hydrates are useful for the biological and pharmacological activities for which venlafaxine and its salts are known in the art. These O-α-acyloxyalkyl ethers may be used in treating or inhibiting central nervous system disorders, including depression, anxiety, panic disorder, post-traumatic stress disorder, late luteal phase dysphoric disorder (also known as pre-menstrual syndrome), attention deficit disorder, with and without hyperactivity, obsessive compulsive disorder, social phobias, generalized anxiety disorder, bulimia nervosa, Gilles de la Tourette Syndrome, Shy Drager Syndrome, vasomotor flushing, drug and alcohol addiction, cocaine addiction, sexual dysfunction (including premature ejaculation), borderline personality disorder, chronic fatigue syndrome, fibromyalgia, urinary incontinence, chronic obstructive pulmonary disorder, migraine, Raynaud's Syndrome, postherpetic neuralgia, pain, chronic back pain, and others. These compounds are also useful in the inducement of cognition enhancement, treatment of obesity and in regimens for cessation of smoking or other tobacco uses.

The compounds of the present invention are further useful for the treatment of senile dementia, Parkinson's Disease, epilepsy, Alzheimer's disease, amnesia, amnesic syndrome, autism, and schizophrenia.

This invention also includes methods of treating, preventing, inhibiting or alleviating each of the maladies listed above in a mammal, preferably in a human, the methods comprising providing a pharmaceutically effective amount of a compound of this invention to the mammal in need thereof.

"Providing" as used herein with respect to providing a compound or substance covered by the invention, means either directly administering such a compound or substance, or administering a prodrug, derivative or analog which forms an equivalent amount of the compound or substance within the body.

A pharmaceutically effective dose will include those doses which provide the relief or prevention sought for the malady in question. The compounds of this invention may be provided in the dosages and pharmaceutical formulations known in the art as useful for venlafaxine hydrochloride (such as those doses known for the venlafaxine hydrochloride products marketed by Wyeth-Ayerst Laboratories under the Effexor® trademark). It will be understood that the initial dose, increases therefrom and final daily administration will be determined by a medical professional considering the needs and conditions for each recipient. For instance, a daily dose for an adult human may be from about 75 mg to about 450 mg per day, preferably between about 75 and about 225 mg per day. An initial dose of 75 mg per day may be administered, with increases as determined by a medical professional.

This invention also includes pharmaceutical compositions comprising a pharmaceutically effective amount of a compound of this invention and one or more pharmaceutically acceptable carriers or excipients. A preferred method of administration includes the use of the present compounds in extended release formulations of the type described in published PCT application WO 99/22724 (Sherman et al.), which is incorporated herein by reference.

The present invention is exemplified, but not limited by, the following specific examples.

EXAMPLE 1

{4-[2-(Dimethylamino)-1-(1-hydroxy cyclohexyl)ethyl]phenoxy}methyl pivalate

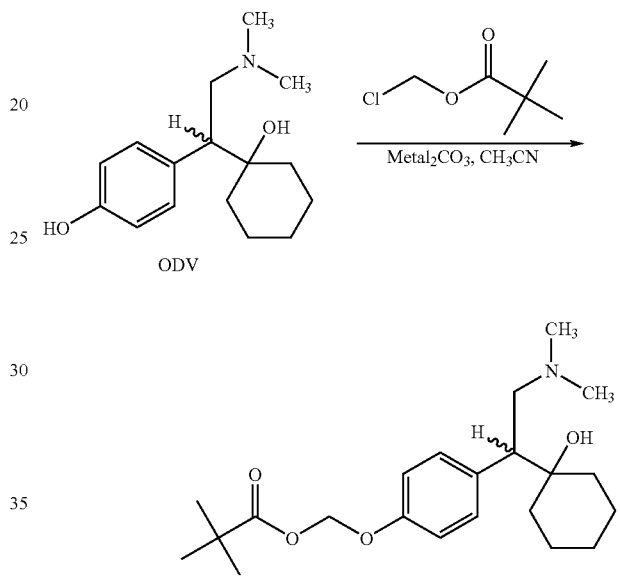

4-[2-(Dimethylamino)-1-(1-hydroxycyclohexyl)ethyl] phenol (1 g, 3.79 mmol), chloromethyl pivalate (0.75 g, 5 mmol), anhydrous $K_2CO_3$ (0.7 g, 5 mmol) and KI (75 mg, 0.5 mmol) were stirred in acetonitrile (50 mL) and refluxed overnight. The solvent was evaporated and the residue was partitioned between ethyl acetate and water. The ethyl acetate was dried ($MgSO_4$) and evaporated to give the title compound as a minor component.

IR (KBr) 1758 $cm^{-1}$.

MS(+)FAB[M+H]$^+$378.3 calcd. For $C_{22}H_{35}NO_4$ 377.

EXAMPLE 2

{4-[2-(dimethylamino)-1-(1-hydroxycyclohexyl) ethyl]phenoxy}methyl pivalate

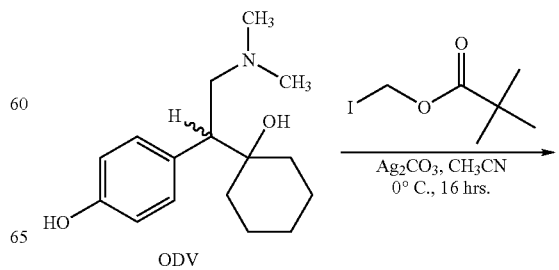

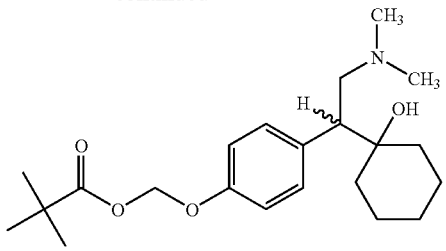

To a solution of ODV (2.0 g, 7.6 mmol) and silver carbonate (8.4 g, 30.4 mmol) in acetonitrile (60 mL) at 0° C. was added a solution of iodomethyl pivalate* (3.4 g, 14.0 mmol) in acetonitrile (100 mL) dropwise over 4 hr. The reaction mixture was filtered through diatomaceous earth (CELITE, Celite Corporation, Lompoc, Calif.), then absorbed onto a activated magnesium silicate (60–100 mesh) (FLORISIL, U.S. Silica Company). and purified by column chromatography (FLORISIL, ethyl acetate: acetonitrile 9:1) to afford the title compound (0.87 g, 45%, based on 68% conversion) as a yellow tinted semi-solid: $^1$H NMR (CD$_3$CN) δ 0.78–1.0 (m, 2H), 1.19 (s, 9H), 1.15–1.35 (m, 4H), 1.4–1.7 (m, 4H), 2.2 (s, 6H), 2.25 (dd, J=11.2, 4.5 Hz, 1H), 2.94 (dd, J=11.2, 4.5 Hz, 1H), 3.22 (t, J=11.2 Hz, 1H), 5.7 (s, 2H), 6.95 (d, J=8.7 Hz, 1H), 7.13 (d, J=8.7 Hz, 1H); $^{13}$C-NMR (CD$_3$CN) δ 22.22, 22.44, 26.91, 27.10 (t), 32.83, 38.78 (t), 39.55 (s), 45.71 (q), 52.58, 61.74, 74.45 (d), 86.78 (t), 116.54, 131.48 (d), 136.68, 156.44, 178.05 (s); MS (EI) m/z 378 (M+H)$^+$; further characterized as the maleate salt. Anal. (C$_{26}$H$_{39}$NO$_8$-0.25H$_2$O) Calc: C, 62.69; H, 7.99; N, 2.81. Found: C, 62.68; H, 7.68; N, 2.65.

The celite cake was taken up in brine and extracted with ethyl acetate. Evaporation of the solvent affords 0.65 g (33%) recovered ODV.

EXAMPLE 3

4-[(1R)-2-(dimethylamino)-1-(1-hydroxycyclohexyl) ethyl]phenyl pivalate

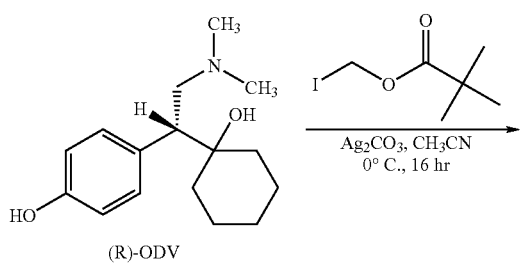

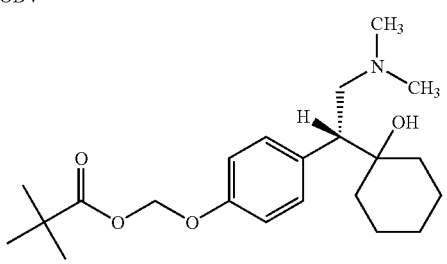

To a solution of ODV (3.0 g, 11.4 mmol) and silver carbonate (12.6 g, 45.6 mmol) in acetonitrile (300 mL) at 0° C. was added a solution of iodomethyl pivalate* (6.9 g, 28.5 mmol) in acetonitrile (40 mL) in eight equal portions over 16 hr. The reaction mixture was filtered through diatomaceous earth (CELITE, Celite Corporation, Lompoc, Calif.), then absorbed onto activated magnesium silicate (60–100 mesh) (FLORISIL, U.S. Silica Company) and purified by column chromatography (FLORISIL, ethyl acetate:acetonitrile 9:1) to afford the title compound (1.15 g, 39%, based on 60% conversion) as a white foam: $^1$H NMR (CD$_3$CN) δ 0.78–1.0 (m, 2H), 1.19 (s, 9H), 1.15–1.35 (m, 4H), 1.4–1.7 (m, 4H), 2.2 (s, 6H), 2.25 (dd, J=11.2, 4.5 Hz, 1H), 2.94 (dd, J=11.2, 4.5 Hz, 1H), 3.22 (t, J=11.2 Hz, 1H), 5.7 (s, 2H), 6.95 (d, J=8.7 Hz, 1H), 7.13 (d, J=8.7 Hz, 1H); $^{13}$C-NMR (CD$_3$CN) δ 22.22, 22.44, 26.91, 27.10 (t), 32.83, 38.78 (t), 39.55 (s), 45.71 (q), 52.58, 61.74, 74.45 (d), 86.78 (t), 116.54, 131.48 (d), 136.68, 156.44, 178.05 (s); [α]$^{20}_D$ -5.95° (c 1.00, MeOH); MS (EI) m/z 378 (M+H)+.

The CELITE cake was taken up in brine and extracted with ethyl acetate.

Evaporation of the solvent affords 1.2 g (40%) recovered ODV.

EXAMPLE 4

4-[(1S)-2-(dimethylamino)-1-(1-hydroxycyclohexyl) ethyl]phenyl pivalate

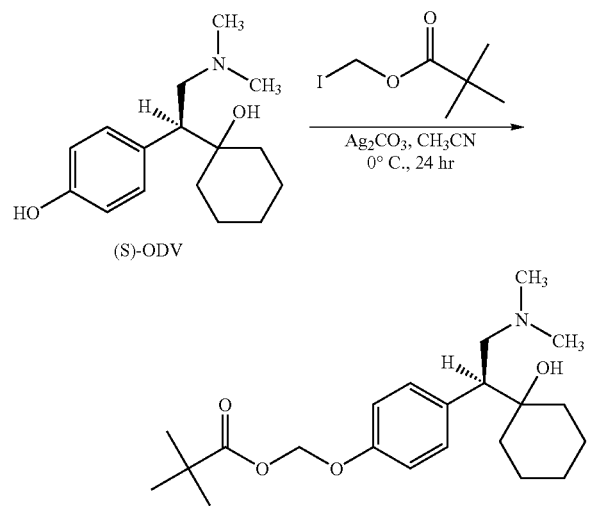

To a solution of ODV (4.0 g, 15.2 mmol) and silver carbonate (16.8 g, 60.8 mmol) in acetonitrile (400 mL) at 0° C. was added a solution of iodomethyl pivalate* (8.3 g, 34.3 mmol) in acetonitrile (150 mL) over a 9 hr period. The reaction mixture was filtered through diatomaceous earth (CELITE, Celite Corporation, Lompoc, Calif.), then absorbed onto activated magnesium silicate (60–100 mesh) (FLORISIL, U.S. Silica Company). and purified by column chromatography (FLORISIL, ethyl acetate:acetonitrile 9:1) to afford the title compound (1.58 g, 48%, based on 57% conversion) as a clear viscous oil: $^1$H NMR (CD$_3$CN) δ 0.78–1.0 (m, 2H), 1.19 (s, 9H), 1.15–1.35 (m, 4H), 1.4–1.7 (m, 4H), 2.2 (s, 6H), 2.25 (dd, J=11.2, 4.5 Hz, 1H), 2.94 (dd, J=11.2, 4.5 Hz, 1H), 3.22 (t, J=11.2 Hz, 1H), 5.7 (s, 2H), 6.95 (d, J=8.7 Hz, 1H), 7.13 (d, J=8.7 Hz, 1H); $^{13}$C-NMR (CD$_3$CN) δ 22.22, 22.44, 26.91, 27.10 (t), 32.83, 38.78 (t), 39.55 (s), 45.71 (q), 52.58, 61.74, 74.45 (d), 86.78 (t), 116.54, 131.48 (d), 136.68, 156.44, 178.05 (s); [α]$^{20}$$_D$+7.23° (c 1.00, MeOH); MS (EI) m/z 378 (M+H)+.

The CELITE cake was taken up in brine and extracted with ethyl acetate.

Evaporation of the solvent affords 1.7 g (43%) recovered ODV.

EXAMPLE 5

{4-[2-(dimethylamino)-1-(1-hydroxycyclohexyl)ethyl]phenoxy}methyl pivalate

Maleate Salt

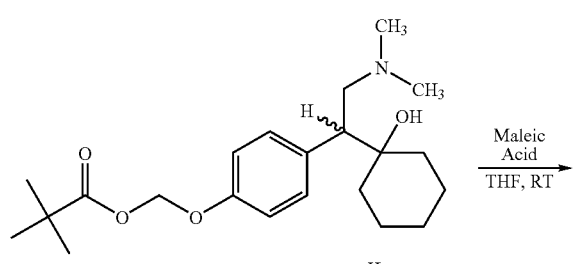

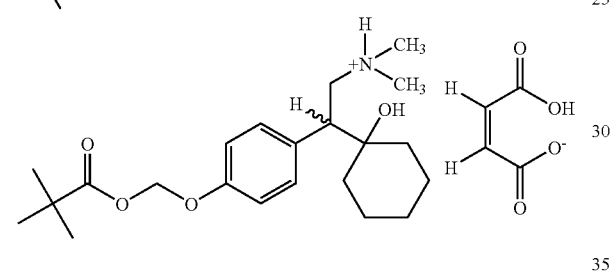

To a solution of {4-[2-(dimethylamino)-1-(1-hydroxycyclohexyl)ethyl]phenoxy}methyl pivalate (0.032 g, 0.085 mmol) prepared as described in Example 1, in THF (1.0 mL) at RT was added a solution of maleic acid (0.007 g, 0.06 mmol) in THF (1.0 mL). The mixture was warmed and diluted with hexane. The solution was cooled and the resulting crystals filtered off giving the desired maleate salt as a white solid: mp 112–113° C., $^1$H NMR (DMSO-d$_6$) δ 0.9–1.6 (m, 10H), 1.13 (s, 9H), 2.7 (br.s, 6H), 2.97 (m, 1H), 3.55 (m, 2H), 4.59 (br.s, 1H), 5.78 (s, 2H), 6.02 (s, 2H), 7.03 (d, J=8.6 Hz, 1H), 7.33 (d, J=8.6 Hz, 1H), 8.4 (br.s, 1H); MS (EI) m/z 378 (M+H)+; (C$_{26}$H$_{39}$NO$_8$·0.25H$_2$O) Calc: C, 62.69; H, 7.99; N, 2.81. Found: C, 62.68; H, 7.68; N, 2.65.

What is claimed is:

1. A compound of the Formula (I):

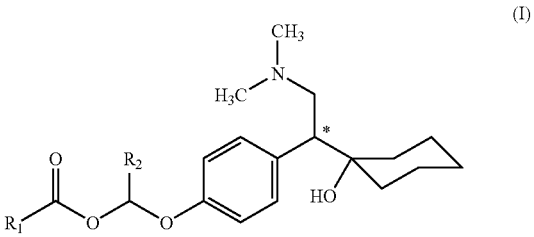

wherein:
the configuration at the steriogenic center (*) may be R, S, or RS (the racemate);
R$_1$ is C$_1$–C$_6$ alkoxy; and
R$_2$ is selected from H, or C$_1$–C$_6$ alkyl; or, pharmaceutically acceptable salt or hydrate thereof.

2. A pharmaceutical composition comprising a pharmaceutically effective amount of a compound of Formula I:

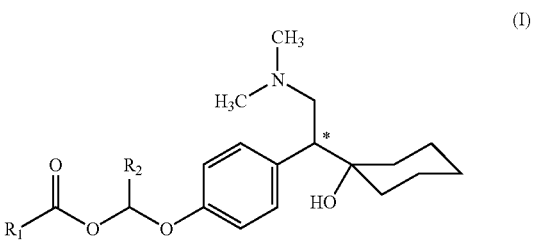

wherein:
the configuration at the steriogenic center (*) may be R, S, or RS (the racemate);
R$_1$ is C$_1$–C$_6$ alkoxy; and
R$_2$ is selected from H, or C$_1$–C$_6$ alkyl; or, pharmaceutically acceptable salt or hydrate thereof; and a pharmaceutically acceptable carrier or excipient.

* * * * *